(12) United States Patent
Chung et al.

(10) Patent No.: US 6,479,192 B1
(45) Date of Patent: Nov. 12, 2002

(54) NON-AQUEOUS ELECTROLYTE FOR ELECTROCHEMICAL SYSTEMS AND LITHIUM SECONDARY BATTERY COMPRISING THE SAME

(75) Inventors: Geun-Chang Chung, Taejeon (KR); Song-Hui Jun, Taejeon (KR); Hyeong-Jin Kim, Taejeon (KR)

(73) Assignee: LG Chemical Ltd., Seoul (KR)

( * ) Notice: Subject to any disclaimer, the term of this patent is extended or adjusted under 35 U.S.C. 154(b) by 0 days.

(21) Appl. No.: 09/582,144

(22) PCT Filed: Jan. 29, 1999

(86) PCT No.: PCT/KR99/00043

§ 371 (c)(1),
(2), (4) Date: Oct. 19, 2000

(87) PCT Pub. No.: WO00/25381

PCT Pub. Date: May 4, 2000

(30) Foreign Application Priority Data

Oct. 23, 1998 (KR) .............................. 98/44507

(51) Int. Cl.$^7$ ............................................. H01M 10/40
(52) U.S. Cl. ........................ 429/338; 429/331; 429/332
(58) Field of Search ................................. 429/330, 331, 429/332, 333, 338

(56) References Cited

U.S. PATENT DOCUMENTS

| | | | | |
|---|---|---|---|---|
| 4,840,858 A | * | 6/1989 | Furukawa et al. | 429/330 |
| 5,472,809 A | * | 12/1995 | Perton et al. | 429/311 |
| 5,643,695 A | * | 7/1997 | Barker et al. | 429/331 |
| 5,891,588 A | * | 4/1999 | Sakai et al. | 429/332 |
| 5,910,381 A | * | 6/1999 | Barker et al. | 429/331 |

FOREIGN PATENT DOCUMENTS

| | | | | |
|---|---|---|---|---|
| EP | 575191 | * | 12/1993 | H01M/10/40 |
| JP | 07-326385 | * | 12/1995 | H01M/10/40 |

OTHER PUBLICATIONS

Chung et al., Chemical Abstract No. 2000–847085, Dec. 2000.*

* cited by examiner

Primary Examiner—Stephen Kalafut
(74) Attorney, Agent, or Firm—Nixon Peabody LLP (57) ABSTRACT

A non-aqueous electrolyte lithium secondary battery that includes: a carbon capable of intercalating and de-intercalating lithium ion as an anode; a lithium containing material that can reversibly intercalate and de-intercalate lithium ion as a cathode; and a non-aqueous electrolyte including trans-4,5, dialkyl-1,3- dioxolane-2-one substantially free of cis-4,5-dialkyl-1,3-dioxolane-2-one and a lithium salt.

8 Claims, 6 Drawing Sheets

NON-AQUEOUS ELECTROLYTE FOR ELECTROCHEMICAL SYSTEMS AND LITHIUM SECONDARY BATTERY COMPRISING THE SAME

CROSS-REFERENCES TO RELATED APPLICATIONS

This application is based on application No. 98-44507 filed in the Korea Industrial Property Office on Oct. 23, 1998, the content of which is incorporated hereinto by reference.

BACKGROUND OF THE INVENTION (a) Field of the Invention

The present invention relates to a non-aqueous electrolyte for electrochemical systems, and more particularly, to a non-aqueous electrolyte for electrochemical systems capable of generating an electromotive force by an action of lithium ion, in conjunction with at least one of the electrodes comprising of carbons with graphite structure.

(b) Description of the Related Art

As technologies in the electronics have been tremendously improved, the use of various portable electronics including the notebook computers and mobile communication devices has become widespread in recent years. As a power source of driving these portable electronics, the demand for secondary batteries has been increased. Although the conventional lead batteries and nickel-cadmium batteries have excellent performances, these aqueous solution type batteries are not satisfactory in weight and energy density. Therefore, non-aqueous electrolyte secondary batteries that can exhibit high voltage and high energy density have been desired.

Non-aqueous electrolyte batteries using lithium or material that can store lithium as their electrode active material have been investigated due to the advantage that lithium is the lightest and also most electropositive metal that can potentially provide high voltage and lightweight energy sources. Lithium secondary batteries are conventionally constituted of a pair of electrodes that can store and emit lithium reversibly; a porous insulating membrane interposed between the electrodes; and a non-aqueous electrolyte comprising a lithium salt and a mixture of aprotic solvents.

By convention, the negative electrode defined as the anode is the more electropositive electrode that is oxidized upon discharge. The positive electrode defined as the cathode is the more electronegative electrode that is reduced upon discharge. Typically lithium ion is released from the negative electrode upon discharge and stored by the positive electrode. For example, U.S. Pat. No. 4,035,555 discloses a battery comprising niobium tetraselenide as positive electrode material, lithium metal as negative electrode material and non-aqueous electrolyte with propylene carbonate (PC) as the solvent. Upon discharge, lithium ion released from the lithium anode is transferred to the cathode to form lithium intercalated niobium tetraselenide. The potential use of various metal oxide and metal chalcogenide as a positive electrode material was reviewed more comprehensively in D. W. Murphy and P. A. Christian, Science, Vol. 205, 1979, page 4407.

As a negative electrode material, lithium metal has been used as a lithium source. Although the lithium metal can provide a high energy density negative electrode, it presents a cycle life problem and a safety concern because of poor lithium plating efficiency and intrinsically high chemical reactivity. Upon repeated cycling, surface of the lithium electrode becomes porous due to dendritic plating of lithium. The formation of such structure with large surface area is undesirable because it reacts violently with moisture and air. Furthermore the battery is assembled as charged state when lithium metal is used as a negative electrode, which also requires special attention to prevent internal or external short circuit in the production of such batteries, especially when the high voltage material is used for the positive electrode. Lithium alloys also present similar problems in the handling of the negative electrode and of the resulting batteries, even though the cycle life and safety can be improved. Furthermore lithium alloys have limited ductility and their uses are severely limited to batteries that do not require much curvature of the electrode.

On the other hand, U.S. Pat. No. 4,423,125 discloses a non-aqueous lithium secondary battery, which comprises a lithiated graphite instead of lithium metal or lithium alloys for the negative electrode. Since this battery uses graphite as a host of lithium storage capable of reversibly intercalating and de-intercalating lithium ions, it exhibits good cycle life characteristics. However, in order to operate in conjunction with a positive electrode that does not contain extractable lithium, the graphite electrode should be prelithiated to be electrochemically active. Such pre-lithiation may present problems because the pre-lithiated graphite is highly reactive to moisture, and because it adds an extra step of intercalating lithium uniformly to the graphite without forming metallic lithium.

As a new cathode active material that contains extractable lithium, U.S. Pat. No. 4,302,518 discloses a lithium-containing transition metal oxide having a layer structure. A secondary lithium battery can be produced by combining this material with a negative electrode comprising of a more electropositive material that is capable of reversibly intercalating and de-intercalating lithium ion. For example, a graphite electrode can be used as such a negative electrode. When graphite or other carbon material is used for an anode, it exhibits good cycle life and improved safety characteristics. Such battery is assembled as inactive state, and thereby requires to be charged in order to be electrochemically active.

One drawback of the carbon anode is the poor Coulombic efficiency at the first cycle, lowering the battery capacity. Therefore, when $LiCoO_2$ is initially used for the positive electrode, the x in $LiCoO_2$ after the first charge-discharge cycle becomes much less than the initial value. Such irreversible capacity arises from the reaction of electrolyte on the carbon surface, and accompanies a consumption of lithium ion that is initially released from the positive electrode. The amount of lithium capacity consumed in the initial charge cycle depends on the composition of non-aqueous electrolyte and the type of anode active material.

Meanwhile, the carbon material is normally divided into amorphous carbons having only partial and short-range order and high-crystalline graphitic carbons with a well-defined long-range crystalline order. The amorphous carbons are advantageous in terms of the interfacial stability toward wide range of electrolytic solvents including conventional cyclic esters such as PC and gamma butyrolactone (γBL). In terms of the energy density, the amorphous carbons are not as satisfactory as the high-crystalline graphitic carbons, due to its low true density. However, if the high-crystalline graphitic carbons are used for the negative electrode in a non-aqueous electrolyte secondary battery containing PC or γ-BL for its electrolyte, the battery is not fully charged, and practical battery performances are not obtained. Such failure is known to arise from the reaction of these electrolytes on the surface of highly crystalline graphitic carbons, as reported for examples in A. N. Dey and B. P. Sullivan, J. Electrochem. Soc., Vol. 117, 1970, page 222 and Fujimoto et al, J. Power Sources, Vol. 63, 1996, page 127.

Thus, to fully utilize the high energy density of the high crystalline graphitic carbons, it is critical to use an appropriate electrolyte. Conventional electrolytes used in non-aqueous electrolyte lithium batteries consist of a mixture of organic solvents and a lithium salt. The requirements for the organic solvent are a capability of dissolving a large amount of lithium salt (or a high dielectric constant) and a capability of conducting the dissolved lithium ion over the operating temperature range of the battery. Examples of a solvent with a high dielectric constant include cyclic esters such as PC, γ-BL, ethylene carbonate (EC), and butylene carbonate (BC, conventionally referring to 1,2-butylene carbonate or in IUPAC name 4-ethyl-1,3-dioxolan-2-one). EC has a large dielectric constant but it cannot conduct lithium ion at ambient temperature because it is solid below 36° C. Many other chemicals with high dielectric constant such as various small molecular anhydrides and 2-oxazolidinone tend to solidify easily at relatively high temperature. Furthermore, solvents with a large dielectric constant solvate lithium ion so strongly that it is co-intercalated into the graphite layers along with the lithium ion, when lithium ion is first intercalated into the graphitic carbons. Such co-intercalation leads to a large irreversibility in the first cycle and, particularly for PC, γ-BL, and BC, it completely prohibits the graphitic carbon from reversibly intercalating lithium ions.

As an example of a solvent mixture that can be used at ambient temperature to reversibly intercalate lithium into graphite after the first cycle, an ECIPC mixture is reported for example in R. Fong et al, J. Electrochem. Soc., Vol. 139, 1990, page 2009. However, such a mixture of EC and PC exhibits a large initial irreversible capacity loss. Hence it is practically not satisfactory as an electrolyte for non-aqueous lithium secondary batteries. It is further reported in Z. X. Shu et al, J. Electrochem. Soc., Vol. 140, 1993, page 922 that a large amount of gas is generated as a result of the irreversible reaction of the electrolyte on graphite surface. Similarly, the electrolytes containing γ-BL or BC are not compatible with graphitic carbon anode and thus cannot provide sufficient battery performances.

Meanwhile electrolyte mixtures consisting of a solvent with high dielectric constant and a solvent with low viscosity have been commonly used in non-aqueous electrochemical systems including capacitors and primary lithium batteries. improved lithium ion conductivity of such mixture is disclosed for example in U.S. Pat. No. 4,957,833 for the mixture of cyclic carbonate and linear carbonate. In particular, in several patents (U.S. Pat. Nos. 5,521,027 and 5,639,575), the mixture comprising EC and linear carbonate is disclosed for lithium secondary batteries consisting of high crystalline graphitic carbons as the negative electrode.

On the other hand, the electrolytes based on the mixture of EC and linear carbonates present a problem for high rate discharge at low temperature, because of high melting temperature of EC. Improved performance at low temperature is disclosed for example in U.S. Pat. No. 5,472,809 for electrolytes comprised of EC, PC and DMC and in U.S. Pat. No. 5,643,695 for mixtures of EC, PC, and linear carbonate, or EC, BC, and linear carbonate. However, due to the reactivity of PC and BC toward high crystalline graphitic carbons, it has a disadvantage that the structure of carbons that can be used for the negative electrode is severely limited to the ones with large surface area.

In view of the above described status of the art, an object of the present invention is to provide a non-aqueous electrolyte containing a solvent with high dielectric constant, where the electrolyte exhibits high conductivity at low temperature and small irreversibility toward a wide range of graphitic carbon anodes.

SUMMARY OF THE INVENTION

It is an object of the present invention to provide a non-aqueous electrolyte for use in electrochemical systems capable of generating an electromotive force by an action of lithium ion.

It is another object of the present invention to provide a non-aqueous electrolyte for use in electrochemical systems capable of generating an electromotive force by an intercalation of lithium ion, in conjunction with at least one of the electrodes comprising of carbons with graphite structure.

These and other objects may be achieved by a non-aqueous electrolyte for electrochemical systems including trans-4,5-dialkyl-1,3-dioxolan-2-one, where two alkyl group are independently having 1 to 2 carbons; and a lithium salt.

The non-aqueous electrolyte lithium secondary battery includes a carbon capable of intercalating and de-intercalating lithium ion for an anode; a lithium containing material that can reversibly intercalate and de-intercalate lithium ion for a cathode; and a non-aqueous electrolyte including trans-4,5-dialkyl-1,3-dioxolan-2-one and a lithium salt.

These and other advantages of the present invention will become apparent to those skilled in the art upon reading and understanding the following description of the preferred embodiments, and accompanying drawings.

BRIEF DESCRIPTION OF THE DRAWINGS

In FIGS. 2–6, "ex." refers to example and "com." refers to comparative example.

DETAILED DESCRIPTION OF THE INVENTION

The present invention provides a non-aqueous electrolyte for use in electrochemical systems capable of generating an electromotive force by an action of lithium ion, and more specifically by an intercalation of lithium ion into carbons with graphite structure. The non-aqueous electrolyte includes a lithium salt and trans-4,5-dialkyl-1,3-dioxolan-2-one of the structure shown in Formula 1.

[Formula 1]

(where the $R_1$ and $R_2$ are independently alkyl groups having 1 to 2 carbon atoms.)

Such electrochemical systems include, in particular, a non-aqueous electrolyte secondary lithium battery including a high crystalline graphitic carbon anode and a positive electrode composed of an active material including an extractable lithium that can reversibly intercalate and de-intercalate lithium.

The electrolyte includes a mixture of non-aqueous solvents including the first, the second, and optionally the third solvents. The first solvent is trans-4,5-dialkyl-1,3-dioxolan-2-one. The second solvents is selected from the group of solvents that can stabilize the interface of graphitic carbon anode, such as EC, chloro-ethylene carbonate, dichloro-ethylene carbonate, fluoro-ethylene carbonate with at least one hydrogen atom substituted by a fluorine atom, vinylene carbonate, and 3-methyl-2-oxazolidinone. The third solvents includes esters selected from the group consisting of diethyl carbonate (DEC), ethyl methyl carbonate (EMC), dimethyl carbonate (DMC), methyl propionate, ethyl propionate, methyl formate, ethyl formate, methyl acetate, ethyl acetate and mixture thereof. Desirably, at least one of the two alkyl groups of the trans-4,5-dialkyl-1,3-dioxolan-2-one is methyl group.

Preferred lithium salt is one selected from the group consisting of lithium hexafluoro phosphate ($LiPF_6$), lithium tetrafluoro borate ($LiBF_4$), lithium hexafluoro arsenate, lithium perchlorate and lithium imide salt with fluoroalkyl-sulfone side chains.

The non-aqueous electrolyte of the present invention is useful for electrochemical systems capable of generating an electromotive force by an action of lithium ion, and more particularly by an intercalation of lithium ion into carbons with graphite structure. Such electrochemical systems include a non-aqueous electrolyte lithium secondary battery with an anode including a high crystalline graphitic carbon. The carbon preferably has a true density of not smaller than 2.1 $g/cm^3$ and not higher than 2.27 $g/cm^3$, an interplanar distance of the (002) plane between 0.335 nm and 0.338 nm, and the specific surface area measured by Brunauer-Emmett-Teller (BET) method between 0.1$m^2$/g and 10 $m^2$/g. The positive electrode for the non-aqueous electrolyte lithium secondary battery can be comprised of any material with an extractable lithium that can reversibly intercalate and de-intercalate lithium. Preferred are lithium containing transition metal oxides. The negative and positive electrodes are assembled in a battery with an insulative porous membrane interposed between the two electrodes. Typically the electrolyte of the present invention is placed such that the electrolyte is completely impregnated in the pore of the membrane as well as the porous network created in the two electrodes.

Additionally, the non-aqueous electrolyte of the present invention can be useful also, for examples, in electrolytic capacitors based on the electrodes comprising a high surface area carbon with graphite structure, which can be operated over a wide voltage windows. By reducing the reactivity of the electrolyte on the electrodes containing carbon with graphite structure, the operating voltage window can be widened to below 0.8 V with reference to lithium electrode, below which conventional electrolytes based on PC start decomposition. Such widening of the operating voltage window is potentially beneficial because more energy can be stored.

Thus, the invention described herein makes possible the objectives of providing a nonaqueous electrolyte that exhibits reduced irreversible reaction with a high crystalline graphitic carbon anode. Such electrolytes are useful in electrochemical systems capable of generating an electromotive force by an action of lithium ion, and more specifically by an intercalation of lithium ion into carbons with graphite structure. The electrolyte of the present invention is particularly useful in providing an improved non-aqueous secondary lithium battery with a large energy density, improved discharge characteristics even at low temperature, long cycle life at and above room temperature.

The non-aqueous electrolyte of the present invention includes a lithium salt and trans-4,5-dialkyl-1,3-dioxolan-2-one. The electrolyte is particularly useful in providing a non-aqueous electrolyte lithium secondary battery with unique advantages of fulfilling simultaneously a satisfactory initial charging characteristics, high rate discharge performance at low temperature and long cycle life, when in conjunction with a high crystalline graphitic carbon anode and a positive electrode containing an extractable lithium that can reversibly intercalate and deintercalate lithium.

Before describing the preferred embodiment, it is useful to understand the problems associated with the conventional electrolytes based on mixtures of EC and PC, which severely limit the type of high crystalline graphitic carbons that can be used for the negative electrode without causing excessive irreversible reaction at the initial cycle.

Generally, high crystalline graphitic carbons used for a negative electrode of lithium secondary battery may be categorized in terms of their crystal structure and morphology. One category contains highly crystalline, anisotropic graphites showing a uniform alignment of graphite layers and flaky morphology. Examples are the SFG and KS series of synthetic graphite manufactured by Timcal, Limited (Switzerland) and natural graphites of flaky morphology as produced for example by Nippon Kokuen (Japan). Another category contains highly polycrystalline artificial graphites produced from pitch as their starting material. Examples are the MCMB series of artificial graphite from Osaka Gas (Japan) and Kawasaki Steel (Japan) produced by the heat treatment of the mesocarbon microbead grown in the matrix of mesophase pitch at around 2800° C., the MCF series of artificial graphites from Petoca (Japan) produced by the heat treatment of the mesophase carbon fiber obtained from the mesophase pitch at around 3000° C., and MP series of artificial graphites from Nippon Carbon (Japan) produced by the heat treatment of the powder derived from bulk mesophase.

It has been known that if lithium is first intercalated electrochemically to a graphitic carbon anode in PC-based electrolytes, propylene carbonate is decomposed on the surface of the graphitic carbon, which results in the generation of gas and the destruction of the graphite structure. It is believed that such destructive reaction between the graphitic carbon and PC originates from the co-intercalation of PC into the graphite layers. Other cyclic carbonates such as BC (referring typically to 1,2-butylene carbonate or to rarely 1,2-butylene carbonate that is a mixture of cis-4,5-dimethyl-1,3-dioxolan-2one and trans-4,5-dimethyl-1,3-dioxolan-2-one) present similar problems due to the similarity of its dielectric constant and molecular geometry to PC.

Through intensive studies on the electrolytes based on mixtures of EC and PC, the present inventors have found that the extent of the irreversible surface reaction by PC is varied depending on the structural characteristics of the graphitic. When the fraction of PC, defined as the volume of PC over the total volume of EC and PC, is increased to 0.4, all artificial graphites derived from pitch showed large increase in the irreversible capacity loss in the first cycle, whereas some flaky graphites showed no changes. The flaky graphites with the specific surface area measured by Brunauer-Emmett-Teller (BET) method larger than 10 in $m^2/g$ was particularly inert to electrolytes based on the mixture of EC and PC, up to a large PC fraction of 0.8. The use of electrolytes based on the mixture of EC and PC in combination with the negative electrode comprising of such flaky graphites are disclosed in U.S. Pat. No. 5,643,695. However, the same electrolyte based on the mixture of EC and PC cannot provide sufficient reversibility in the initial cycle for other carbons derived from pitch or for flaky graphites with BET area of not larger than 6 in $m^2/g$.

The flaky graphites with BET area larger than 6 $m^2/g$ has much lower bulk density of typically smaller than 0.4 $g/cm^3$, than the other graphites, which typically have bulk density of typically 0.8 $g/cm^3$. Practically, however, a carbon with high bulk density and small surface area is desirable because an electrode can be produced with less binder and less solvent, when the electrode is prepared by coating the slurry comprising of the binder polymer and an appropriate solvent for dissolving the binder.

Thus, to fully utilize a wider range of high crystalline graphitic carbons especially with a large bulk density and a small surface area, a solvent similar to PC in high dielectric constant and improved low temperature conductivity, but showing much reduced reactivity to high crystalline graphitic carbons is desired.

The present inventors have found that the reactivity of a solvent with a high dielectric constant can be drastically reduced by modifying the structure of PC such that the approach of the solvent to the graphite layers are sterically hindered. Specifically the present inventors have found that a solvent with the general chemical structure of trans-4,5-dialkyl-1,3-dioxolan-2-one with the two alkyl group having independently one or two carbon atoms, shows dramatically reduced reactivity toward high crystalline graphitic carbon anodes, without a decrease in dielectric constant. In this case, the nature of improvement is believed to originate from the specific structure of the solvent.

Hence, other solvents with similar or even identical chemical formula do not show the same improvement unless the steric hindrance is operative. For example, 1,2-butylene carbonate, 1,2-butylene carbonate, cis-4,5-dimethyl-1,3-dioxolan-2-one and trans-4,5-dimethyl-1,3-dioxolan-2-one are the constitutional isomers with the same chemical formula, but only the trans-4,5-dimethyl-1,3-dioxolan-2-one exhibits a reduced reactivity toward high crystalline graphitic carbon anodes. The present inventors have also found that the electrolyte containing trans-4,5-dialkyl-1,3-dioxolan-2-one exhibit a capability of dissolving a large amount of lithium salt and improved conductivity at low temperature.

Therefore, the electrolyte of the present invention has unique advantages of fulfilling simultaneously a satisfactory initial charging characteristics, high rate discharge performance at low temperature and long cycle life, when a battery is prepared using a high crystalline graphitic carbon anode and a positive electrode containing an extractable lithium that can reversibly intercalate and de-intercalate lithium.

The non-aqueous electrolyte lithium secondary battery of the present invention is preferably constituted of a negative electrode comprising of a high crystalline graphitic carbon, a positive electrode comprising of a material containing an extractable lithium with a capability of reversibly intercalating and de-intercalating lithium, and nonaqueous electrolyte comprising of a lithium salt and a mixed solvent containing trans-4,5-dialkyl-1,3-dioxolan-2-one.

The preferred material for the negative electrode is a high crystalline graphitic carbon, having a true density of not smaller than 2.1 $g/cm^3$ and an interplanar distance of the (002) plane between 0.335 nm and 0.338 nm. The preferred anode material can be further characterized by the BET area between 0.1 $m^2/g$ and 10 $m^2/g$ and the average diameter of the carbon powder being not smaller than 1 $\mu m$.

The preferred material for the positive electrode is a lithium containing transition metal oxides, expressed by a general formula $Li_xMO_2$ with M indicating at least one of Co, Ni and Mn, and x being $0.5 < x < 1.1$.

The preferred electrolyte of the present invention includes a mixture of non-aqueous solvents including a first solvent, trans-4,5-dialkyl-1,3-dioxolan-2-one, a second solvent and optionally a third solvent.

The second solvent may be selected from a group of solvents that can stabilize the interface of graphitic carbon anode, such as EC, chloro-ethylene carbonate, dichloro-ethylene carbonate, fluoro-ethylene carbonate with at least one hydrogen atom substituted by a fluorine atom, vinylene carbonate, and 3-methyl-2-oxazolidinone. The third solvent may be ester solvents selected from the group consisting of, diethyl carbonate (DEC), ethyl methyl carbonate (EMC), dimethyl carbonate (DMC), methyl propionate, ethyl propionate, methyl formate, ethyl formate, methyl acetate, ethyl acetate and mixture thereof.

Desirably, at least one of the two alkyl groups of the trans-4,5-dialkyl-1,3-dioxolan-2-one is methyl group. Preferred lithium salt is one selected from the group consisting of lithium hexafluoro phosphate ($LiPF_6$), lithium tetrafluoro borate ($LiBF_4$), lithium hexafluoro arsenate, lithium perchlorate and lithium imide salt with fluoroalkylsulfone side chains.

In one embodiment, the mixture of solvents comprises: (1) trans-4,5-dimethyl-1,3-dioxolan-2-one; (2) EC; and (3) an organic carbonate solvent selected from the group consisting of DEC, EMC, DMC and mixture thereof. It is preferred that the EC is present in an amount by volume fraction of 5% or larger. The total amount of the cyclic carbonate is preferably between 30% and 70% by volume for typical polyolefin separators, but can be even larger for separators with improved wettability. Preferred inorganic lithium salt is lithium hexafluoro phosphate, lithium tetrafluoro borate and the mixture thereof.

In another embodiment, the mixture of solvents comprises: (1) trans-4-ethyl-5-methyl,3-dioxolan-2-one; (2) EC; and (3) an organic carbonate solvent selected from the group consisting of DEC, EMC, DMC and mixture thereof. It is preferred that the EC is present in an amount by volume fraction of 5% or larger. The total amount of cyclic carbonate solvent is preferably between 30% and 65% by volume for typical polyolefin separators, but can be even larger for separators with improved wettability. Preferred inorganic lithium salt is lithium hexafluoro phosphate, lithium tetrafluoro borate and the mixture thereof.

Figure 1:
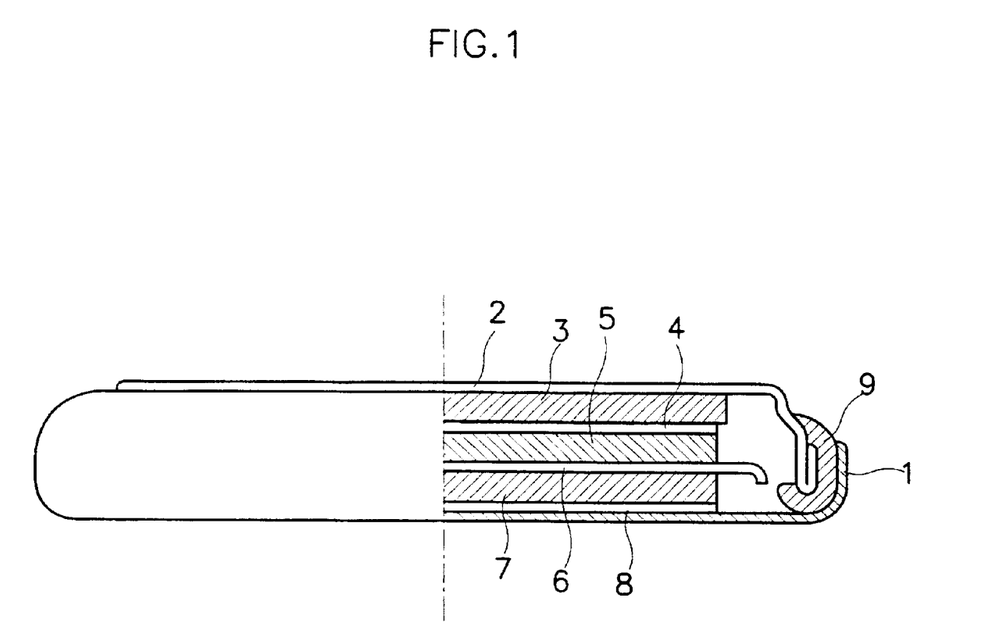
FIG. 1 is a cross-sectional view showing a typical structure of a coin type battery according to the present invention.

FIG. 1 shows a typical structure of a coin type non-aqueous lithium secondary battery of the present invention. The battery case 1 and a sealing plate 2 are both made of stainless steel. An anode 5 is a composite of active material and binder polymer adhered onto the current collector 4 made of copper foil. The metallic spacer 3 made of copper is place on top of the anode current collector to ensure good electronic contact between the anode and the case. A separator 6 is a microporous membrane made of polyolefin having a void structure. A cathode 7 is a composite of active material, conductive carbon and binder polymer adhered onto the current collector 8 made of aluminum foil. After the electrodes and the separator are completely impregnated with electrolyte, the battery is sealed with gasket 9 made of polypropylene.

Example 1

Preparation of the First Solvent

The trans-4,5-dimethyl-1,3-dioxolan-2-one is prepared by the ester exchange reaction of diethyl carbonate with d, 1-2,3-butanediol in the presence of sodium. All reaction is carried out under the atmosphere of nitrogen, and all reagents and solvents are dried, for example, using activated silica prior to the reaction.

In 250 ml tetrahydrofuran solvent, 9.0 g of (2R, 3R)-(-)-butanediol and 5 g of sodium is added. The solvent mixture is heated gradually until sodium is completely melted. The mixture is cooled down slowly to ambient temperature and 10.7 g of diethyl carbonate is slowly added over a period of 1 hour. The resulting mixture is brought up to 80° C. and kept for 6 hours at that temperature. The completion of the reaction is checked by gas chromatography. After the completion of the reaction, the mixture is cooled down to ambient temperature.

The resulting mixture is distilled at reduced pressure until the volume is reduced in half. Then, water is added into the resulting mixture and it is neutralized using a dilute aqueous hydrochloric acid solution. The extractions are performed using ethyl ether, and the combined organic phases are washed using 10% aqueous sodium carbonate solution. The organic phase is further purified by drying the ethyl ether phase with anhydrous sodium sulfate and subsequently filtering the mixture. The pure trans-4,5-dimethyl-1,3-dioxolan-2-one (7 g/60%) is obtained by removing low boiling residues by distillation.

270 MHz $^1$H-NNM (CDCl$_3$) δ: 1.46 (6H, m, 2 Me's), 4.34 (2H, m, 2 CH's)

Manufacturing of a Lithium Secondary Battery

A coin-type half cell with analogous construction to the battery shown in FIG. 1 was made using a negative electrode 5 based on P15BG (BET area=0.77 m$^2$/g, true density 2.15 g/cm, (002) layer spacing=0.3367 nm), a graphitic carbon from Nippon Carbon (Japan) and a lithium metal counter electrode replacing the cathode 7 and cathode current collector 8.

A solvent was prepared as follows by mixing trans-4,5-dimethyl-1,3-dioxolan-2-one, EC and DEC in the volume ratio of 30:20:50. As a solute for the electrolyte, lithium hexafluoro phosphate was used to form 1 M electrolyte.

Comparative Example 1

A lithium secondary battery was manufactured by the same procedure as in Example 1 except that an electrolytes including PC, EC and DEC in the volume ratio of 30:20:50 was used.

The capacity of these lithium secondary battery of example 1 and comparative example 1 were determined by the following method.

Figure 2:
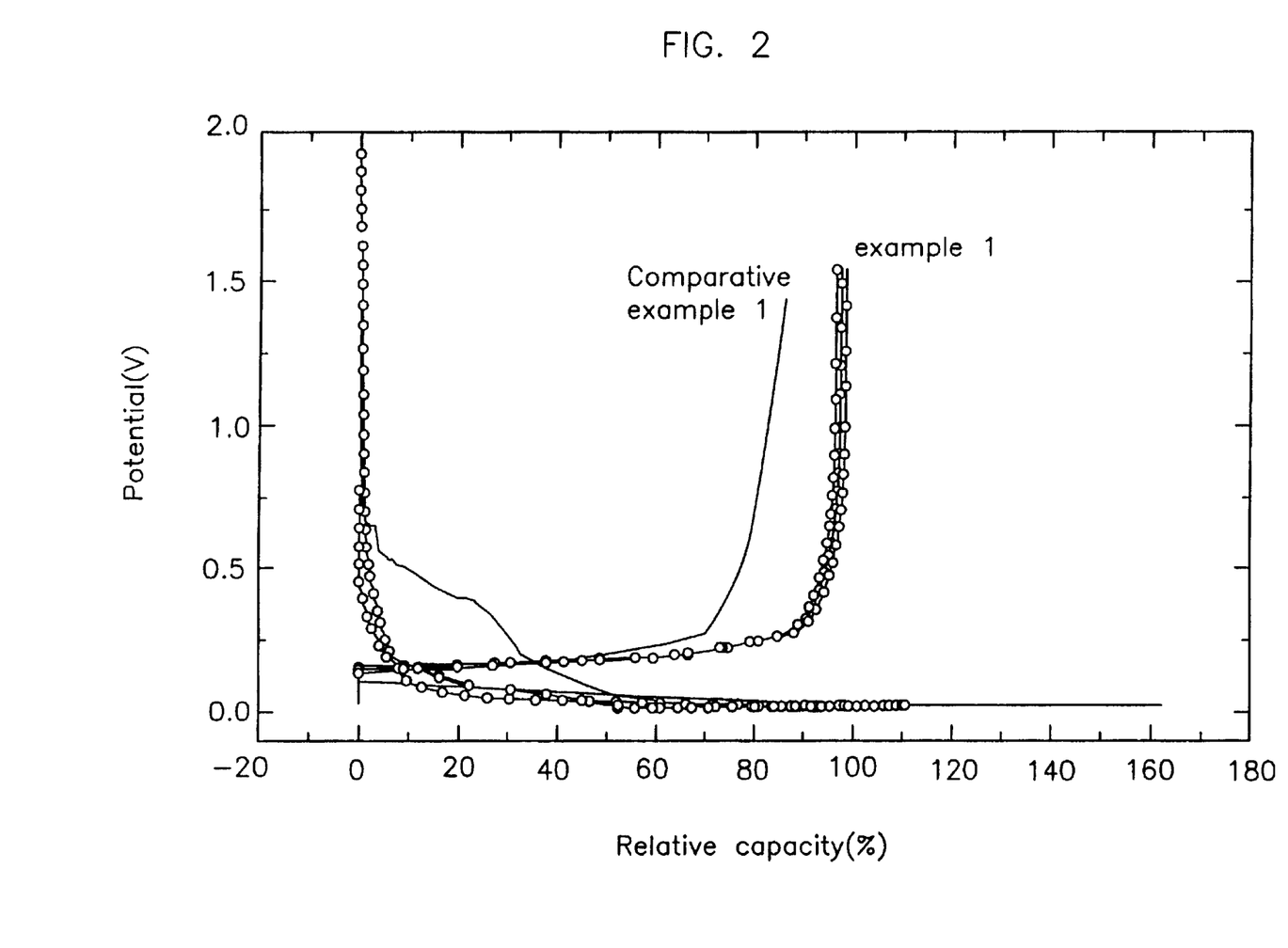
FIG. 2 is a graph showing the initial voltage profile of P15BG from the test in Example 1 and Comparative Example 1.

The intercalation and de-intercalation of lithium to the carbon anode was repeated 5 times under the conditions that the cut-off voltages were 10 mV and 1.5 V, respectively with reference to lithium electrode. The test were performed at 23° C. The results are shown in FIG. 2. The first three cycles are shown for the example 1 but only the first cycle result is shown for the comparative example 1. The capacity of 100% corresponds to the standard reversible capacity of the carbon measured using 1 M LiPF$_6$ solution of 50/50 volume mixture of EC/DEC.

As shown in FIG. 2, the electrolyte based on trans-4,5-dimethyl-1,3-dioxolan-2-one of the present invention exhibits a substantially smaller irreversible reaction with the graphitic carbon anode including P15BG than PC based electrolyte.

EXAMPLES 2–6

Lithium secondary batteries were prepared by the same procedure in Example 1 except that volume ratio of trans-4,5-dimethyl-1,3-dioxolan-2-one, EC and DEC were changed as the following volume ratio. The same test as Example 1 was performed for electrolytes based on trans-4,5-dimethyl-1,3-dioxolan-2-one, EC and DEC with the following volume ratio. The EC fraction is defined as the ratio of the volume of EC and the volume of all the cyclic carbonate, namely, EC and trans-4,5-dimethyl-1,3-dioxolan-2-one in this examples.

Example 2 trans-4,5-dimethyl-1,3-dioxolan-2-one:EC:DEC=50:0:50 (EC fraction=0.0)

Example 3 trans-4,5-dimethyl-1,3-dioxoian-2-one:EC:DEC=40:10:50 (EC fraction=0.2)

Example 4 trans-4,5-dimethyl-1,3-dioxolan-2-one:EC:DEC=30:20:50 (EC fraction=0.4)

Example 5 trans-4,5-dimethyl-1,3-dioxolan-2-one:EC:DEC=20:30:50 (EC fraction=0.6)

Example 6 trans-4,5-dimethyl-1,3-dioxolan-2-one:EC:DEC=10:40:50 (EC fraction=0.8)

Comparative Examples 2–4

Lithium secondary batteries were prepared by the same procedure in Example 1 except that volume ratio of PC, EC and DEC were changed as the following volume ratio.

The same test as Example 1 was performed for electrolytes based on PC, EC and DEC with the following volume ratio. The EC fraction is defined as the ratio of the volume of EC and the volume of all the cyclic carbonate, namely, EC and PC in these comparative examples.

| | |
|---|---|
| Comparative example 2 | PC:EC:DEC = 50:0:50 (EC fraction = 0.0) |
| Comparative example 3 | PC:EC:DEC = 30:20:50 (EC fraction = 0.2) |
| Comparative example 4 | PC:EC:DEC = 20:30:50 (EC fraction = 0.6) |

Figure 3:
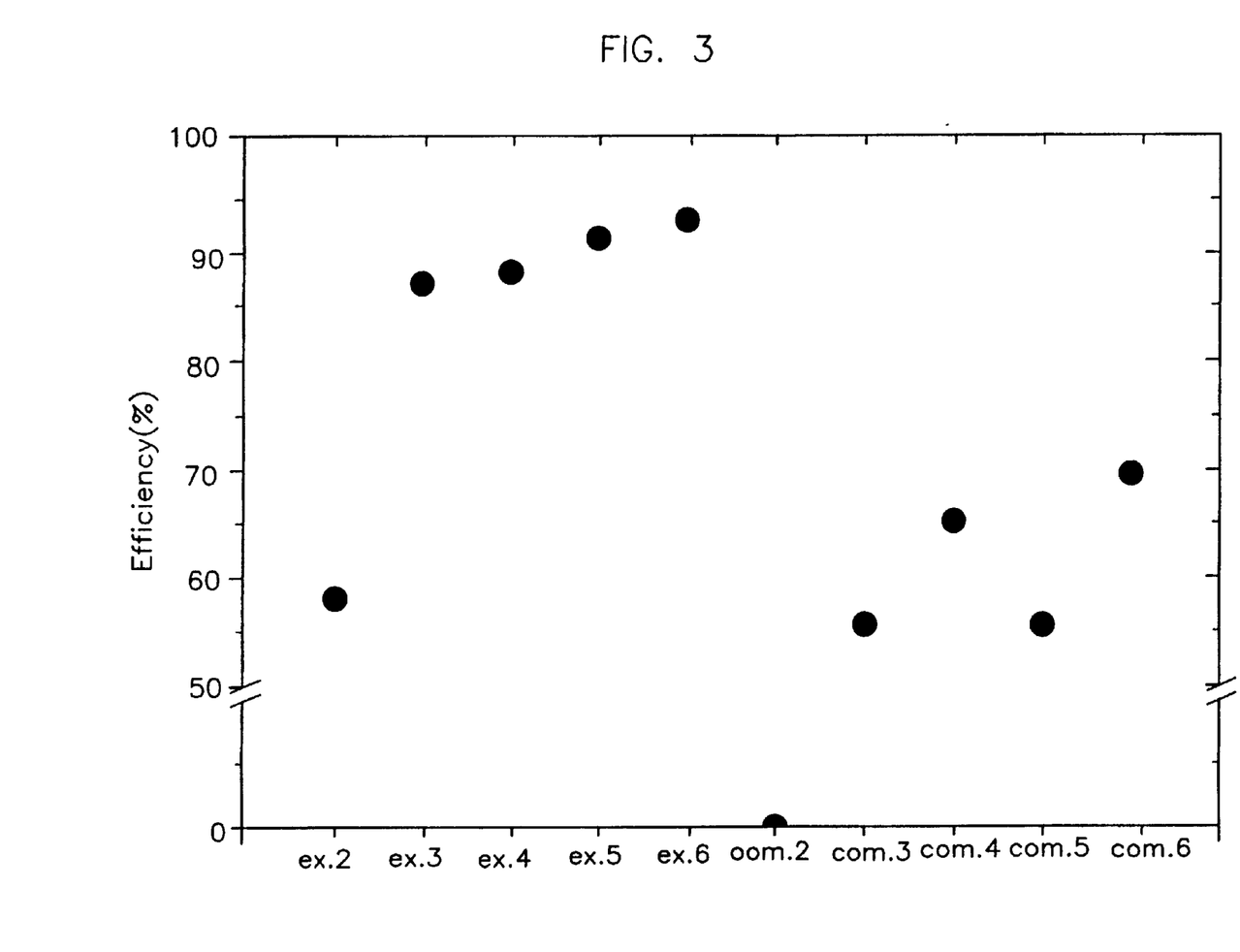
FIG. 3 is a graph showing the irreversible capacity of P15BG from the test in Examples 2–6 and Comparative Examples 2–6.

The Coulombic efficiency of the first cycle defined as the ratio of the de-intercalation capacity and the intercalation capacity of examples 2–6 and comparative examples 24 is plotted in FIG. 3.

Comparative Examples 5–6

Preparation of the First Solvent

The cis-4,5-dimethyl-1,3-dioxolan-2-one was prepared in an identical procedure described in Example 1 except that a commercial 2,3-butanediol comprising 70% meso-form and 30% d, I form was used instead of (2R, 3R)-(−)-butanediol. The resulting product mixture is distilled to obtain the cis-4,5-dimethyl-1,3-dioxolan-2-one.

(bp 80° C./1 mmHg); 270 MHz $^1$H-NMR (CDCl$_3$) δ: 1.37 (6H, m, 2 Me's), 4.85 (2H, m, 2 CH's)

The same test as Example 1 was performed for electrolytes based on cis-4,5-dimethyl1,3-dioxolan-2-one with the following volume ratio.

| | |
|---|---|
| Comparative example 5 | cis-4,5-dimethyl-1,3-dioxolan-2-one:EC:DEC = 30:20:50 (EC fraction = 0.4) |
| Comparative example 6 | cis-4,5-dimethyl-1,3-dioxolan-2-one:EC:DEC = 10:40:50 (EC fraction = 0.8) |

The Coulombic efficiency of the first cycle is plotted in FIG. 3. From the results obtained in Examples 1–6 and Comparative examples 1–6, as shown in FIGS. 2 and 3. It is noted that the electrolyte based on trans-4,5-dialkyl-1,3-dioxolan-2-one of the present invention exhibits a substantially smaller irreversible reaction with the graphitic carbon anode comprising P15BG than either PC based electrolytes or cis-4,5-dimethyl-1,3-dioxolan-2-one.

EXAMPLES 7–11

Comparative Examples 7 to 9

The coin-type half cells was prepared exactly as in Example 1 except that MCMB 10–28 (BET area=2.3 m$^2$/g, true density=2.2 g/cm$^3$, (002) layer spacing=0.336 nm) from Osaka Gas (Japan) was used as an active material for the graphitic carbon anode. The same test as Example 1 was performed for electrolytes based on trans-4,5-dimethyl-1,3-dioxolan-2-one and PC, for electrolytes as used in Examples 2 to 6 and comparative examples 2 to 4.

Figure 4:
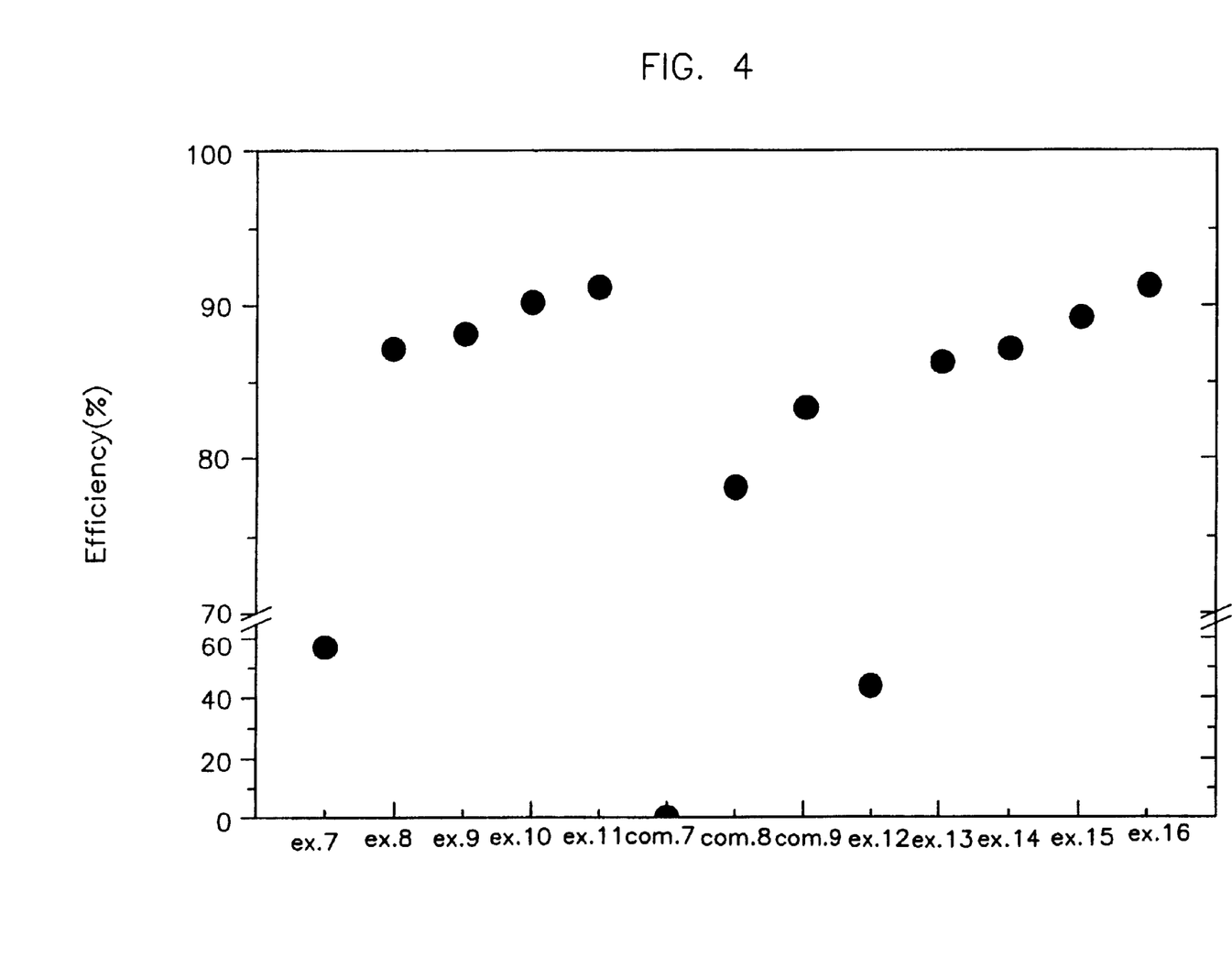
FIG. 4 is a graph showing the irreversible capacity of MCMB 10-28 from the test in Examples 7–16 and Comparative Examples 7–9.

The Coulombic efficiency of the first cycle is plotted in FIG. 4.

EXAMPLES 12–16

Preparation of the First Solvent

The trans-4ethyl-5-methyl-1,3-dioxolan-2-one was prepared in an identical procedure described in Example 1 except that threo-2,3-pentanediol was used instead of d,l-2,3-butanediol.

The same test as Example 7 was performed for electrolytes based on trans-4-methyl-5ethyl-1,3-dioxolan-2-one with the following volume ratio.

Example 12 trans-4-ethyl-5-methyl-1,3-dioxolan-2-one:EC:DEC=50:0:50 (EC fraction 0.0)

Example 13 trans-4-ethyl-5-methyl-1,3-dioxolan-2-one:EC:DEC=40:10:50 (EC fraction=0.2)

Example 14 trans-4-ethyl-5-methyl-1,3-dioxolan-2-one:EC:DEC=30:20:50 (EC fraction=0.4)

Example 15 trans-4-ethyl-5-methyl-1,3-dioxolan-2-one:EC:DEC=20:30:50 (EC fraction=0.6)

Example 16 trans-4-ethyl-5-methyl-1,3-dioxolan-2-one:EC:DEC=10:40:50 (EC fraction=0.8)

The Coulombic efficiency of the first cycle is plotted in FIG. 4.

EXAMPLE 17–21

Comparative Example 10–12

The coin-type half cells was prepared exactly as in Example 1 except that SFG-44 (BET area=4.2 m$^2$/g, true density=2.26 g/cm$^3$, (002) layer spacing=0.3355 nm) from Timcal (Switzerland) is used for the graphitic carbon anode. The same test as Example 1 was performed for electrolytes based on trans-4,5-dimethyl-1,3-dioxolan-2-one and PC with the electrolytes as used in Examples 2 to 6 and Comparative examples 2 to 4.

Figure 5:
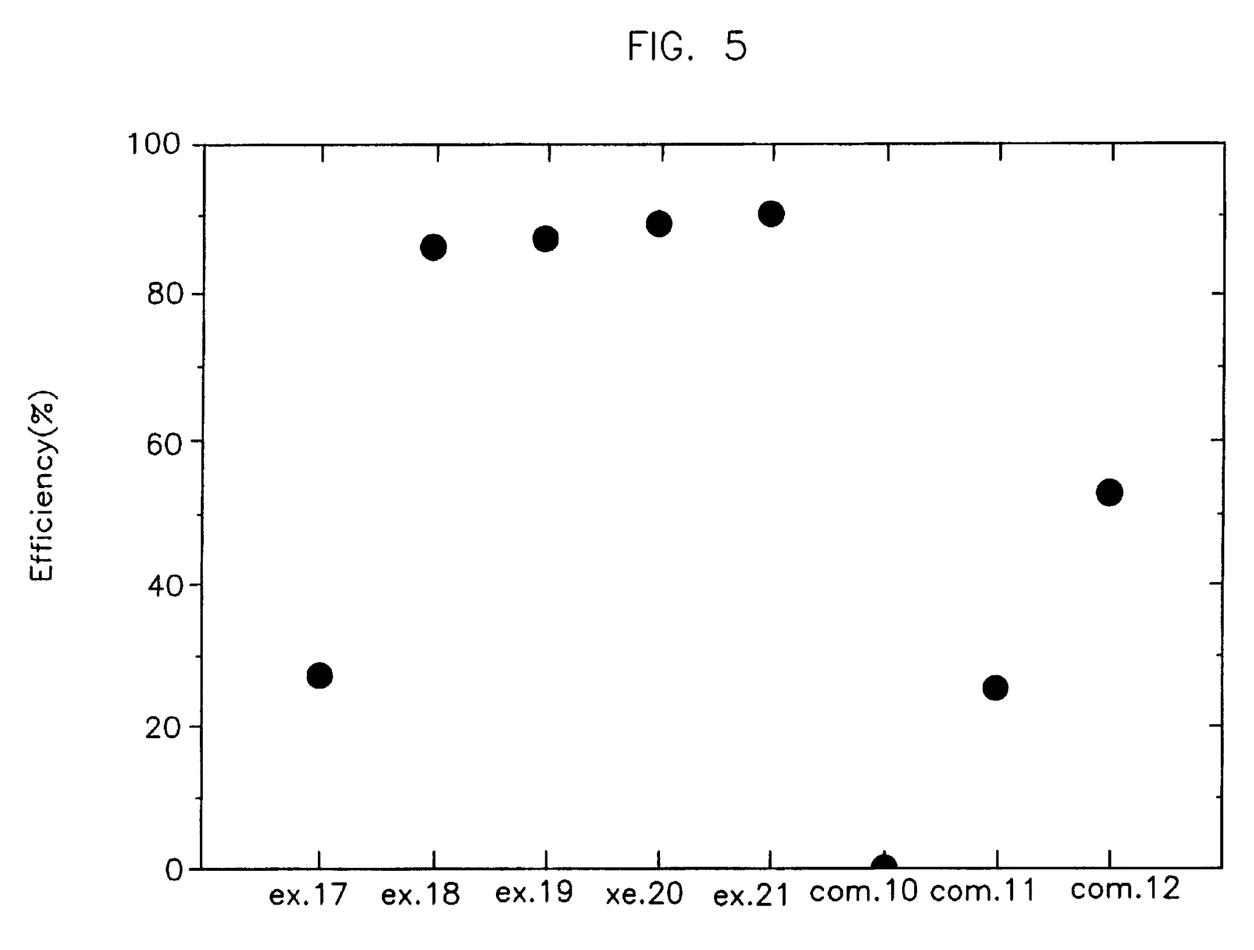
FIG. 5 is a graph showing the irreversible capacity of SFG-44 from the test in Examples 17–21 and Comparative Examples 10–12.

The Coulombic efficiency of the first cycle is plotted in FIG. 5.

From Examples 1 through 21 and Comparative Examples 1 to 12, it is noted that the electrolytes based on trans-4,5-dialkyl-1,3-dioxolan-2-one show sufficiently low irreversibility at the first cycle for a wide range of mixing ratio and for electrodes based on a variety of high crystalline graphitic carbons with diverse structure. For a non-aqueous electrolyte lithium secondary battery comprising of a positive electrode material containing extractable lithium, such an improvement in the irreversibility results in the increased battery capacity.

Therefore, it is apparent from the comparison with PC-based electrolytes that an electrolyte based on trans-4,5-dialkyl-1,3-dioxolan-2-one is advantageous in obtaining a non-aqueous electrolyte lithium secondary battery with high energy density. It can be also understood from the comparison with electrolytes based on PC and cis-4,5-dimethyl-1,3-dioxolan-2-one that the reduced irreversibility from the electrolytes based on trans-4,5-dialkyl-1,3-dioxolan-2-one is due to the unique molecular geometry of trans-4,5-dialkyl-1,3-dioxolan-2-one prohibiting excessive reaction with high crystalline graphitic carbon anodes.

EXAMPLES 22–23

The same test as Example 7 was performed for electrolytes based on the following mixtures of trans-4,5-dimethyl-1,3-dioxolan-2-one. As a solute for the electrolyte, lithium hexafluoro phosphate was used to form 1 M electrolyte.

Example 22; trans-4,5-dimethyl-1,3-dioxolan-2-one:3-methyl-2-Oxazolidinone:DEC=40:10:50

Example 23; Trans-4,5-dimethyl-1,3-dioxolan-2-one:Chloroethylene carbonate:DEC=40:10:50

The lithium intercalation was reversible after the first cycle, and the Coulombic efficiency at the initial cycle was shown in TABLE 1. By way of comparison, results from the electrolyte of example 2 containing no additional solvent with a high dielectric constant and the electrolyte of example 3 containing EC were also shown.

TABLE 1

| | Efficiency (1$^{st}$ cycle) |
|---|---|
| Example 2(None) | 57% |
| Example 3(EC) | 87% |
| Example 22 (3-methyl-2-Oxazolidinone) | 82% |
| Example 23 (Chloroethylene carbonate) | 86% |

From Examples 22 and 23, it is noted that the cycling efficiency of the graphitic carbon anode can be substantially improved by having a solvent capable of stabilizing the interface of the graphitic carbon anode, such as EC, chloro-ethylene carbonate, dichloro-ethylene carbonate, fluoro-ethylene carbonate with at least one hydrogen atom substituted by a fluorine atom, vinylene carbonate, and 3-methyl-2-oxazolidinone.

EXAMPLES 24–29

A coin type non-aqueous lithium secondary battery was made using MCMB 10-28 as an active material for the negative electrode and $LiCoO_2$ as an active material for the positive electrode. With the previously prepared electrolytes based on trans-4,5-dimethyl-1,3-dioxolan-2-one and trans-4-ethyl-5-methyl-1,3-dioxolan-2-one the following batteries are prepared. As a solute for the electrolyte, lithium hexafluoro phosphate was used to form 1 M electrolyte.

Example 24 trans-4,5-dimethyl-1,3-dioxolan-2-one:EC:DEC=40:10:50

Example 25 trans-4,5-dimethyl-1,3-dioxolan-2-one:EC:DEC=30:20:50

Example 26 trans-4,5-dimethyl-1,3-dioxolan-2-one:EC:DEC=10:40:50

Example 27 trans-4-ethyl-5-methyl-1,3-dioxolan-2-one:EC:DEC=40:10:50

Example 28 trans-4-ethyl-5-methyl-1,3-dioxolan-2-one:EC:DEC=30:20:50

Example 29 trans-4-ethyl-5-methyl-1,3-dioxolan-2-one:EC:DEC=10:40:50

Comparative Examples 13–15

Coin type non-aqueous lithium secondary batteries were prepared by the same procedure example 24 except that electrolytes including PC, EC and DEC

| Comparative example 13 | PC:EC:DEC = 30:20:50 |
| Comparative example 14 | PC:EC:DEC = 10:40:50 |
| Comparative example 15 | EC:DEC = 50:50 |

The charge-discharge cycles were repeated 10 times at 25° C., at a constant current corresponding to C/2 rate. The discharge is stopped at 2.5 V, and the charging is switched from a constant current mode to a constant voltage mode at 4.1 V. The total charging time was 3 hours, including the constant current and constant voltage charging modes. The discharge capacity at the 10th cycle is shown in TABLE 2.

After the 11th charging, the temperature is decreased to −20° C. and the batteries were kept for 10 hours at that temperature prior to discharging. The discharging capacity at 20° C. was also measured at C/2 rate. The ratio of the discharge capacity at −20° C. and at 25° C. was shown in TABLE 2. The $Q_d$ (−20° C.) and $Q_d$ (25° C.) are the discharge capacities obtained at −20° C. and 25° C., respectively.

TABLE 2

| | 10th Discharge Capacity (mAh) | $Q_d(-20°\ C.)/Q_d(25°\ C.)$ |
|---|---|---|
| Example 24 | 3.89 | 58.6 |
| Example 25 | 4.09 | 53.2 |
| Example 26 | 4.14 | 12.2 |
| Example 27 | 3.97 | 40.3 |
| Example 28 | 4.08 | 32.5 |
| Example 29 | 4.19 | 11.4 |
| Comparative example 13 | 3.19 | 57.2 |
| Comparative example 14 | 3.78 | 12.5 |
| Comparative example 15 | 4.06 | 2.7 |

From the results shown in Table 2, it is noted that the reversible capacity of the coin type battery is large for batteries based on the Mixtures showing a large Coulombic efficiency at the first cycle. Therefore, the batteries based on the electrolytes containing trans-4,5-dialkyl-1,3-dioxolan-2-one are comparable to the batteries based on the prior art electrolyte EC/DEC and much superior to the batteries based on the prior art electrolyte EC/PC/DEC.

At low temperature, the batteries of the present invention still showed a large discharge utilization or the ratio, $Q_d$ (−20° C.)/$Q_d$ (25° C.), comparable to those based on the prior art electrolyte EC/PC/DEC, and much superior to the batteries based on the prior art electrolyte EC/DEC.

EXAMPLES 30 to 39

Figure 6:
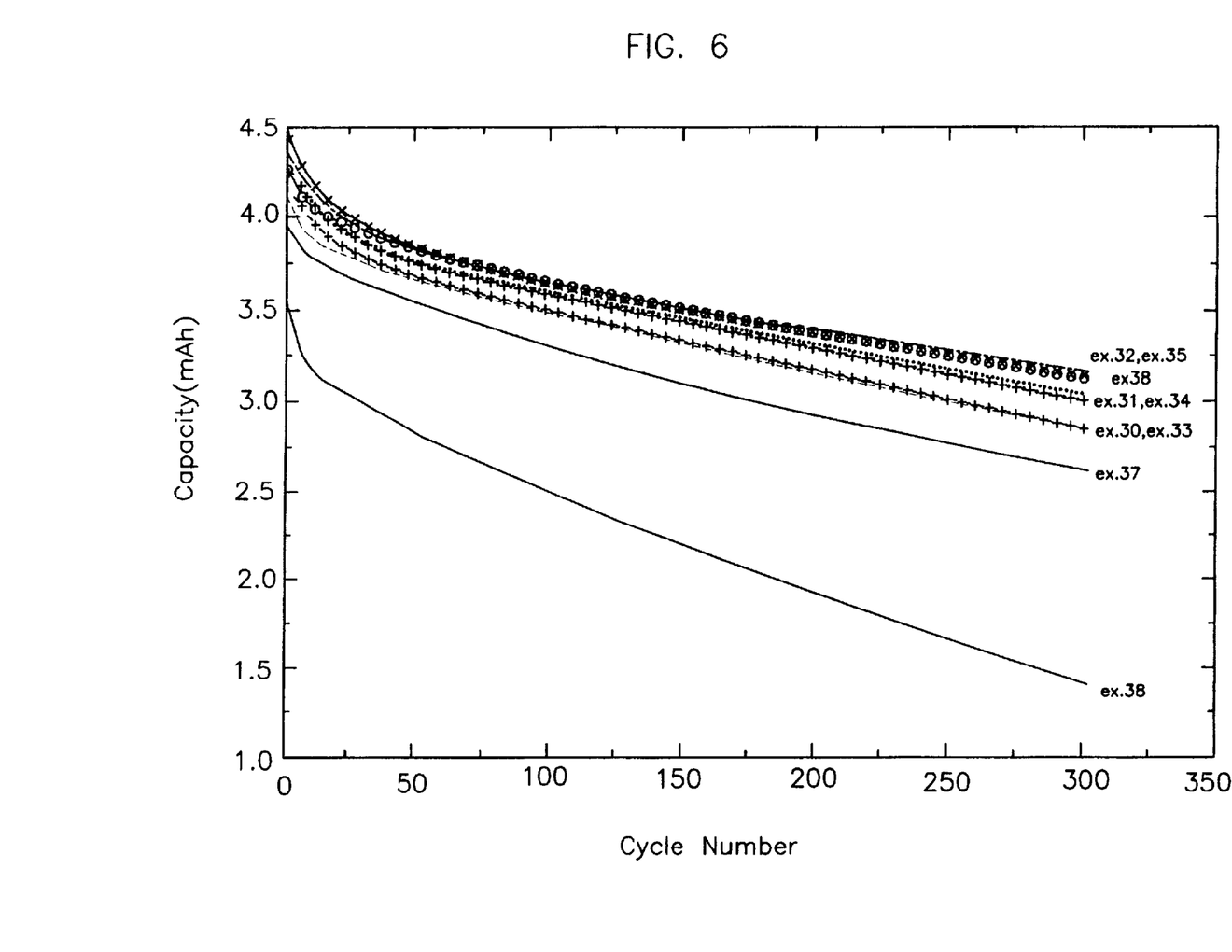
FIG. 6 is a graph showing the long term cycle life at 25° C. from the test in Examples 30 to 39.

The coin type batteries with the same constituent as in Example 24 were made for long term cycling test at 25° C. The charge-discharge cycles were repeated for 300 times, at a constant current corresponding to C/2 rate. The discharge is stopped at 3 V, and the charging is switched from constant current mode to constant voltage mode at 4.1 V. The total charging time was 3 hours, including the constant current and constant voltage charging modes. The results are shown in FIG. 6.

The electrolytes containing trans-4,5-dialkyl-1,3-dioxolan-2-one exhibit a satisfactory cycling performance for a wide range of mixing ratios, with only slight decrease in the initial capacity compared to the EC/DEC electrolyte of the prior art. Compared to EC/PC/DEC electrolytes of the prior art, the electrolytes containing trans-4,5-dialkyl1,3-dioxolan-2-one exhibit superior performance in terms of the initial capacity and the capacity retention during repeated cycling.

As is clear from the above explanation, the non-aqueous electrolyte based on trans-4,5-dialkyl-1,3-dioxoian-2-one provides unique advantages in simultaneously fulfilling a satisfactory initial charging characteristics, high rate discharge performance at low temperature and long cycle life, in conjunction th a negative electrode comprising a high crystalline graphitic carbon and a positive electrode comprising a lithium containing material capable of reversibly intercalating and de-intercalating lithium.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:
1. A non-aqueous electrolyte lithium secondary battery comprising:

a carbon capable of intercalating and de-intercalating lithium ion as an anode;

a lithium containing material that can reversibly intercalate and de-intercalate lithium ion as a cathode; and a non-aqueous electrolyte including trans-4,5-dialkyl-1,3-dioxolane-2-one substantially free of cis-4,5-dialkyl-1,3-dioxolane-2-one and a lithium salt.

2. The non-aqueous electrolyte lithium secondary battery according to claim 1, wherein said carbon is a high crystalline graphitic carbon, characterized by a true density of 2.1 to 2.27 g/cm, an interplanar distance of the (002) plane between 0.335 nm and 0.338 nm, BET area between 0.1 $m^2/g$ and 10 $m^2/g$ and the average diameter of the carbon powder of not smaller than 1 µm.

3. The non-aqueous electrolyte lithium secondary battery according to claim 2 wherein said non-aqueous electrolyte comprises a lithium salt and a first solvent comprising trans-4,5-dialkyl-1,3-dioxolane-2-one; a second solvent selected from a the group consisting of ethylene carbonate, chloro-ethylene carbonate, dichloro-ethylene carbonate, fluorethylene carbonate with at least one hydrogen atom substituted by a fluorine atom, vinylene carbonate, and 3-methyl-2-oxazolidinone; and, optionally a third solvent selected from the group consisting of diethyl carbonate, ethyl methyl carbonate, dimethyl carbonate, methyl propionate, ethyl propionate, methyl formate, ethyl formate, methyl acetate, ethyl acetate and mixture thereof.

4. The non-aqueous electrolyte lithium secondary battery according to claim 1 wherein said lithium containing material for cathode is at least one selected from the group consisting of $LiCoO_2$, $LiNiO_2$, $LiMn_2O_4$, $LiNiVO_4$, $LiCoVO_4$, $LiNi_xCo_{1-x}O_2$, wherein $0<x<0.5$ and mixture thereof.

5. The non-aqueous electrolyte lithium secondary battery according to claim 2 wherein said lithium salt is at least one selected from the group consisting of lithium hexafluoro phosphate ($LiPF_6$), lithium tetrafluoro borate ($LiBF_4$), lithium hexafluoro arsenate, lithium perchlorate and lithium imide salt with fluoroalkylsulfone side chains.

6. The non-aqueous electrolyte lithium secondary battery according to claim 2 wherein said non-aqueous electrolyte comprises a solvent mixture of the trans-4,5-dialkyl-1,3-dioxolane-2-one; ethylene carbonate; and a linear carbonate selected from the group consisting of diethyl carbonate, ethyl methyl carbonate, dimethyl carbonate and mixture thereof, wherein the amount of ethylene carbonate is at least 5% by volume and the amount of a linear carbonate is between 30% and 75% in volume.

7. The non-aqueous electrolyte lithium secondary battery according to claim 9 wherein the lithium salt dissolved in the said solvent mixture is lithium hexafluoro phosphate ($LiPF_6$), lithium tetrafluoro borate ($LiBF_4$), or a mixture thereof.

8. The non-aqueous electrolyte lithium secondary battery according to claim 6 wherein said non-aqueous electrolyte comprises 50 to 70% by volume of a solvent mixture of trans-4,5-dialkyl-1,3-dioxolane-2-one and ethylene carbonate.

\* \* \* \* \*